US009763651B2

(12) United States Patent
Hsiao et al.

(10) Patent No.: US 9,763,651 B2
(45) Date of Patent: Sep. 19, 2017

(54) TENDON STRIPPER

(71) Applicant: E-DA HOSPITAL, Kaohsiung (TW)

(72) Inventors: Chih-Kun Hsiao, Kaohsiung (TW);
Yuan-Kun Tu, Kaohsiung (TW);
Teng-Yao Yang, Kaohsiung (TW);
Feng-Chen Kao, Kaohsiung (TW);
Yi-Jung Tsai, Kaohsiung (TW);
Hao-Yuan Hsiao, Kaohsiung (TW)

(73) Assignee: E-Da Hospital, Kaohsiung (TW)

( * ) Notice: Subject to any disclaimer, the term of this patent is extended or adjusted under 35 U.S.C. 154(b) by 304 days.

(21) Appl. No.: 14/686,914

(22) Filed: Apr. 15, 2015

(65) Prior Publication Data

US 2016/0270771 A1    Sep. 22, 2016

(30) Foreign Application Priority Data

Mar. 18, 2015 (TW) .............................. 104108626 A

(51) Int. Cl.
*A61B 17/32* (2006.01)
*A61B 17/00* (2006.01)
*A61B 17/3205* (2006.01)

(52) U.S. Cl.
CPC .. *A61B 17/00008* (2013.01); *A61B 17/32053* (2013.01); *A61B 2017/00473* (2013.01); *A61B 2017/00477* (2013.01)

(58) Field of Classification Search
CPC ........ A61B 17/00008; A61B 17/32053; A61B 2017/00477; A61B 2017/00473
USPC ....................................................... 606/185
See application file for complete search history.

(56) References Cited

U.S. PATENT DOCUMENTS

| 2003/0125735 | A1* | 7/2003 | Herzon | A61B 18/085 606/51 |
| 2007/0288055 | A1* | 12/2007 | Lee | A61B 17/00008 606/209 |
| 2008/0009895 | A1* | 1/2008 | Pokomey | A61B 17/32002 606/185 |
| 2009/0264871 | A1* | 10/2009 | Merced-O'Neill | A61B 17/00008 606/1 |

FOREIGN PATENT DOCUMENTS

CN          203539414 U    4/2014

* cited by examiner

*Primary Examiner* — Todd J Scherbel
*Assistant Examiner* — Son Dang
(74) *Attorney, Agent, or Firm* — Alan D. Kamrath; Kamrath IP Lawfirm, P.A.

(57) ABSTRACT

A tendon stripper includes a stripping device and a rod. The stripping device includes a stripping member and at least one coupling member coupling to the stripping member. The stripping member has a blade portion and a separating portion separating the stripping member into several parts. The rod has a handle end and a coupling end opposite to the handle end. The coupling end couples to the coupling member of the stripping device. The separating portion allows the stripping member to be divided into first and second parts, and the first and second parts can be combined to each other to jointly receive the tendon. This avoids the generation of the incisions during the tendon transplantation. In addition, since the tendon stripper does not require any instrument for retaining the free end of the tendon, a convenient surgical procedure is provided.

10 Claims, 8 Drawing Sheets

TENDON STRIPPER

BACKGROUND OF THE INVENTION

1. Field of the Invention

The present invention generally relates to a tendon stripper and, more particularly, to a tendon stripper capable of reducing the generation of the incisions during the tendon transplantation.

2. Description of the Related Art

When a tendon of a human body is torn apart or becomes damaged, the associated muscle part will not be able to function properly. In this regard, the breaking parts of the tendon can be joined back to regain the function of the muscle. However, the damaged tendon will have to be removed from the human body if the tendon is dead or cannot be joined. In this case, the damaged tendon should be replaced by a new tendon through an autologous or heterologous tendon transplantation.

During the modern tendon transplantation, a conventional tendon stripper 9 as shown in FIG. 1 is adapted to strip the damaged tendon from a bone. The tendon stripper 9 includes a rod 91 and a handle 92. The rod 91 has a first end 911 and a second end 912 opposite to the first end 911. The first end 911 couples to the handle 92. The second end 912 has a stripping member 913. During the tendon transplantation, the tendon that is connected to a bone is extended through the stripping member 913. Then, the handle 92 is pulled to move the rod 91 along the bone, thereby stripping the tendon off the bone.

When using such a traditional tendon stripper, one end of the tendon must be cut open to form a free end of the tendon, and, then, the free end of the tendon can extend through the stripping member 913 for stripping of the tendon. However, cutting the tendon will increase the amount of incisions, leading to a larger possibility of wound infection. Moreover, since the free end of the tendon must be fixed in place by an instrument during the stripping operation of the tendon, the surgical procedure is complex.

SUMMARY OF THE INVENTION

It is therefore the objective of this invention to provide a tendon stripper which avoids the generation of the incisions during the tendon transplantation, thus lowering the possibility of wound infection.

It is another objective of this invention to provide a tendon stripper which does not need to cut the tendons and form the free ends of the tendons before the stripping operation of the tendon, thus simplifying the surgical procedure.

In one embodiment of the invention, a tendon stripper including a stripping device and a rod is disclosed. The stripping device includes a stripping member and at least one coupling member coupling to the stripping member. The stripping member has a blade portion and a separating portion separating the stripping member into first and second parts. The rod has a handle end and a coupling end opposite to the handle end. The coupling end couples to the coupling member of the stripping device.

In the form shown, the first part has a first extending end and a first assembly end opposite to the first extending end, and the second part has a second extending end and a second assembly end opposite to the second extending end. The first extending end couples to the second extending end, and the first assembly end couples to the second assembly end, to form the stripping member as an enclosed structure.

In the form shown, the first part has a first engaging portion, and the second part has a second engaging portion engaging with the first engaging portion.

In the form shown, the number of the at least one coupling member is two, including a first coupling member and a second coupling member. The first coupling member couples to the first assembly end of the first part, and the second coupling member couples to the second assembly end of the second part. The stripping device couples to the rod via the first coupling member and the second coupling member.

In the form shown, the first coupling member has a first surface, and the second coupling member has a second surface aligned with and connected to the first surface.

In the form shown, the first surface of the first coupling member has a positioning protrusion, and the second surface of the second coupling member has a positioning cavity. The positioning protrusion of the first surface is inserted into the positioning cavity of the second surface.

In the form shown, the first coupling member of the stripping device has a first thread, and the second coupling member of the stripping device has a second thread. The first coupling member and the second coupling member couple together to the coupling end of the rod via the first thread and the second thread.

In the form shown, the coupling end of the rod has a first threaded hole. The first coupling member and the second coupling member are screwed together into the first threaded hole of the coupling end of the rod via the first thread and the second thread.

In the form shown, the sod has a fixing member with a first end and a second end opposite to the first end. The fixing member has a second threaded hole extending from the first end to the second end. The coupling end of the rod has a third thread. The coupling end of the rod, the first coupling member and the second coupling member are screwed together into the fixing member.

In the form shown, the second assembly has a first extending portion protruding from the second assembly, and the coupling end of the rod has a second extending portion protruding from the coupling end. A shoulder portion is formed at the coupling end. The first extending portion abuts with the shoulder portion, and the second extending portion abuts with the first coupling member.

In the form shown, the stripping device includes an auxiliary member with an auxiliary hole extending through the auxiliary member. The first coupling member and the second coupling member couple together to the auxiliary member via the auxiliary hole.

In the form shown, the auxiliary hole has an auxiliary thread.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
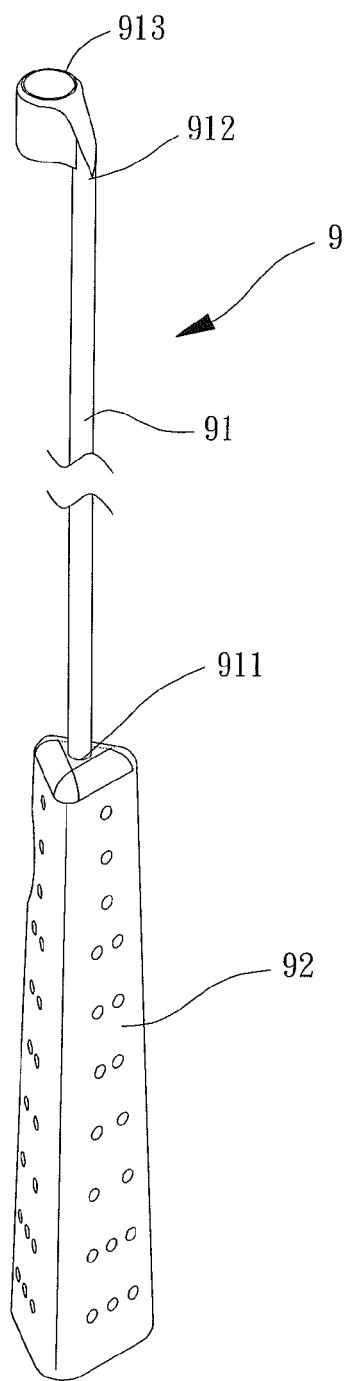
FIG. 1 is a diagrammatic view of a conventional tendon stripper.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 2:
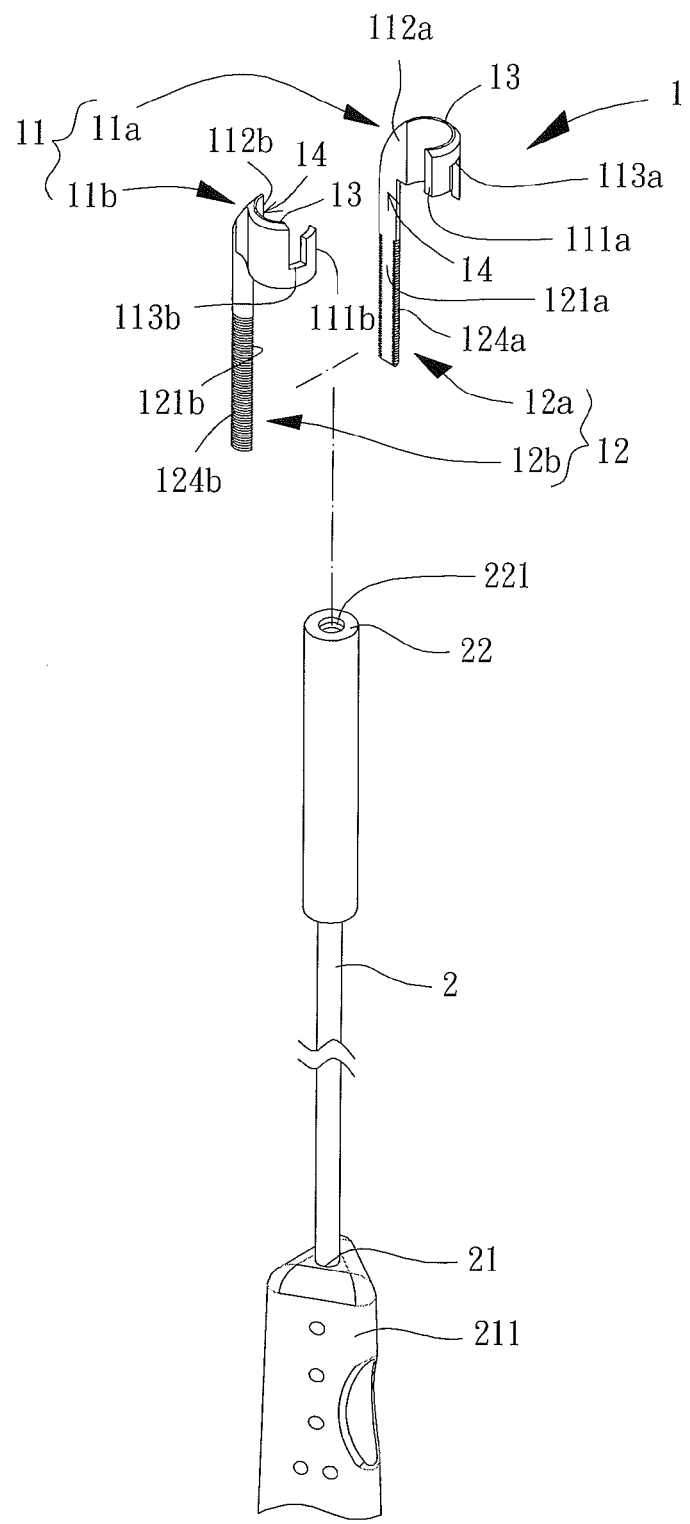
FIG. 2 is an exploded view of a tendon stripper according to a first embodiment of the present invention.

Referring to FIG. 2, a tendon stripper according to a first embodiment of the present invention includes a stripping device 1 and a rod 2. The stripping device 1 couples to one end of the rod 2.

Figure 3:
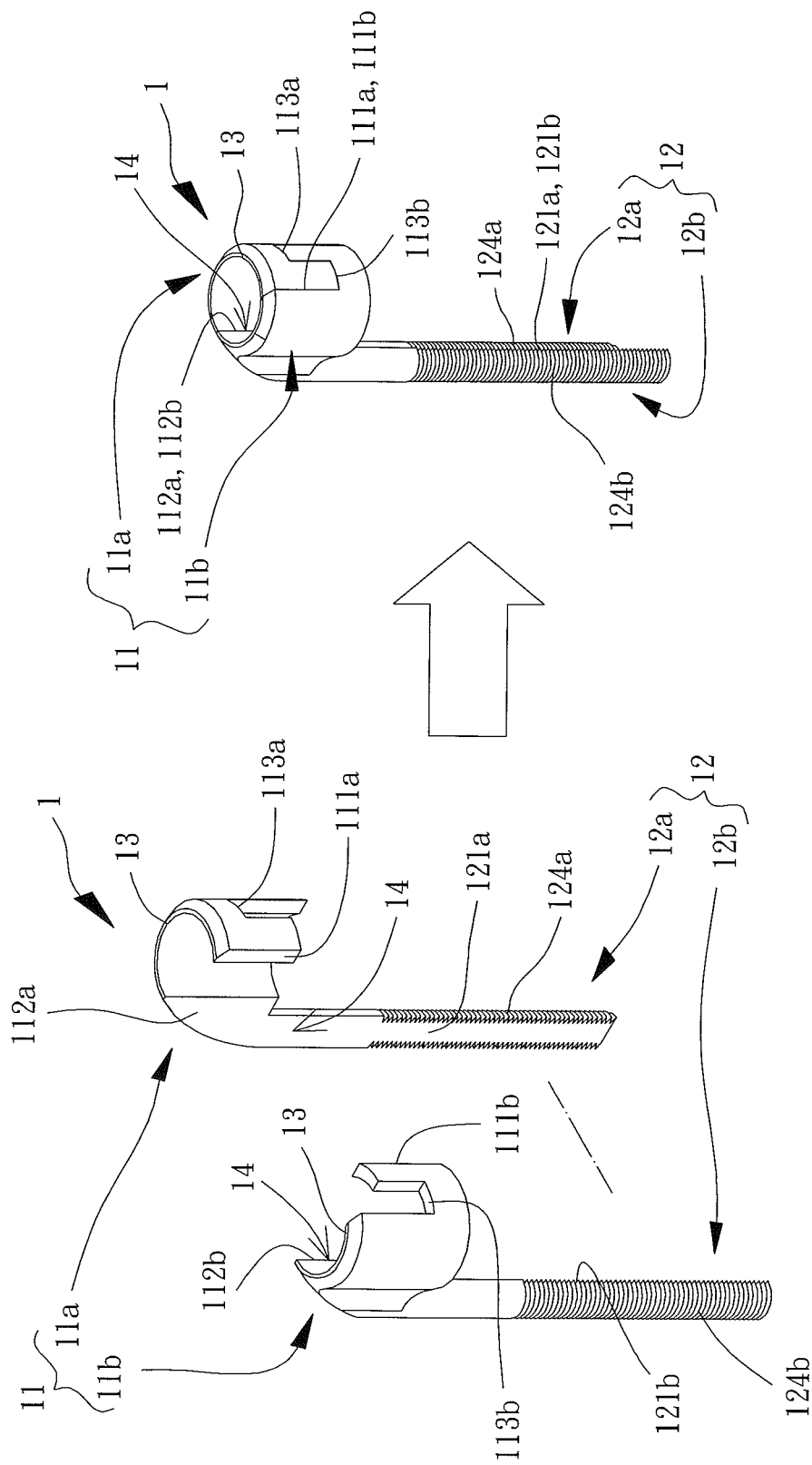
FIG. 3 is an exploded view of a stripping device of the tendon stripper according to the first embodiment of the present invention.

The stripping device 1 includes a stripping member 11 and at least one coupling member 12 coupled to the stripping member 11. The stripping member 11 can be in an enclosed structure with any shape, such as a circular or rectangular shape. In this embodiment, the stripping member 11 is preferably in a circular shape in order not to form any acute part that damages the adjacent muscle tissues during the stripping operation of the tendon. Referring to FIG. 3, the stripping member 11 has a blade portion 13 and a separating portion 14. The blade portion 13 can be an independent blade that requires assembly or can be formed by milling one end of the stripping member 11, which can be appreciated by a person having ordinary skill in the art. In this embodiment, the blade portion 13 is formed by milling one end of the stripping member 11 to reduce the manufacturing cost of the tendon stripper.

The separating portion 14 is adapted to divide the stripping member 11 into several parts. In this embodiment, the stripping member 11 is divided into a first part 11a and a second part 11b by the separating portion 14. Both the first and second parts 11a and 11b include semicircular cross sections. Specifically, the first part 11a has a first extending end 111a and a first assembly end 112a opposite to the first extending end 111a. Similarly, the second part 11b has a second extending end 111b and a second assembly end 112b opposite to the second extending end 111b. Once the first and second parts 11a and 11b are connected to each other, the first extending end 111a abuts with the second extending end 111b, and the first assembly end 112a abuts with the second assembly end 112b, forming the stripping member 11 as an enclosed structure.

Moreover, in this embodiment, a first engaging portion 113a can be included between the first extending end 111a and the first assembly end 112a, and a second engaging portion 113b can be included between the second extending end 111b and the second assembly end 112b. The first engaging portion 113a can engage with the second engaging portion 113b to properly fix the first and second parts 11a and 11b to each other.

Figure 4:
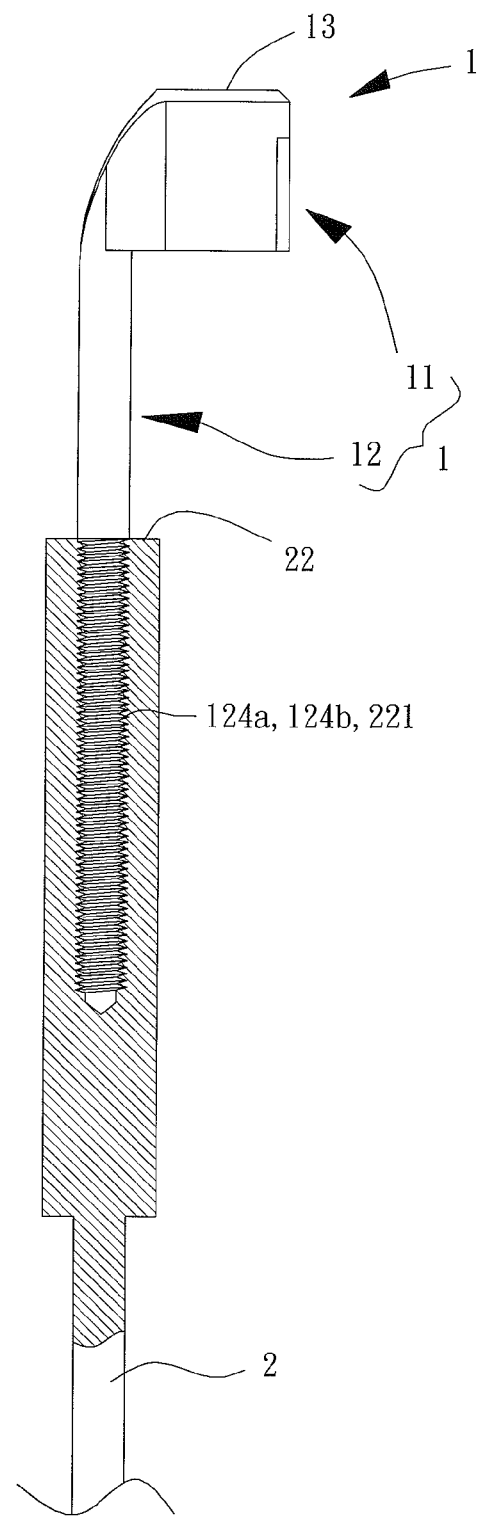
FIG. 4 is a cross-sectional view of the tendon stripper according to the first embodiment of the present invention.

The quantity of the at least one coupling member 12 can be one, and the coupling member couples to the first part 11a or the second part 11b. Alternatively, the quantity of the at least one coupling member 12 can be larger than one. In this embodiment, the quantity of the at least one coupling member is two, including a first coupling member 12a and a second coupling member 12b. Referring to FIGS. 3 and 4, the first and second coupling members 12a and 12b connect with each other, and the assembled first and second coupling members 12a and 12b is then coupled to the rod 2, improving the coupling effect between the stripping device 1 and the rod 2.

Specifically, referring to FIGS. 3 and 4, the first coupling member 12a couples to the first assembly end 112a of the first part 11a, and the second coupling member 12b couples to the second assembly end 112b of the second part 11b. Moreover, the first coupling member 12a has a first surface 121a, and the second coupling member 12b has a second surface 121b. When the first and second parts 11a and 11b are connected with each other, the first surface 121a abuts with the second surface 121b. Thus, the assembled first and second parts 11a and 11b can be coupled to one end of the rod 2.

Figure 5:
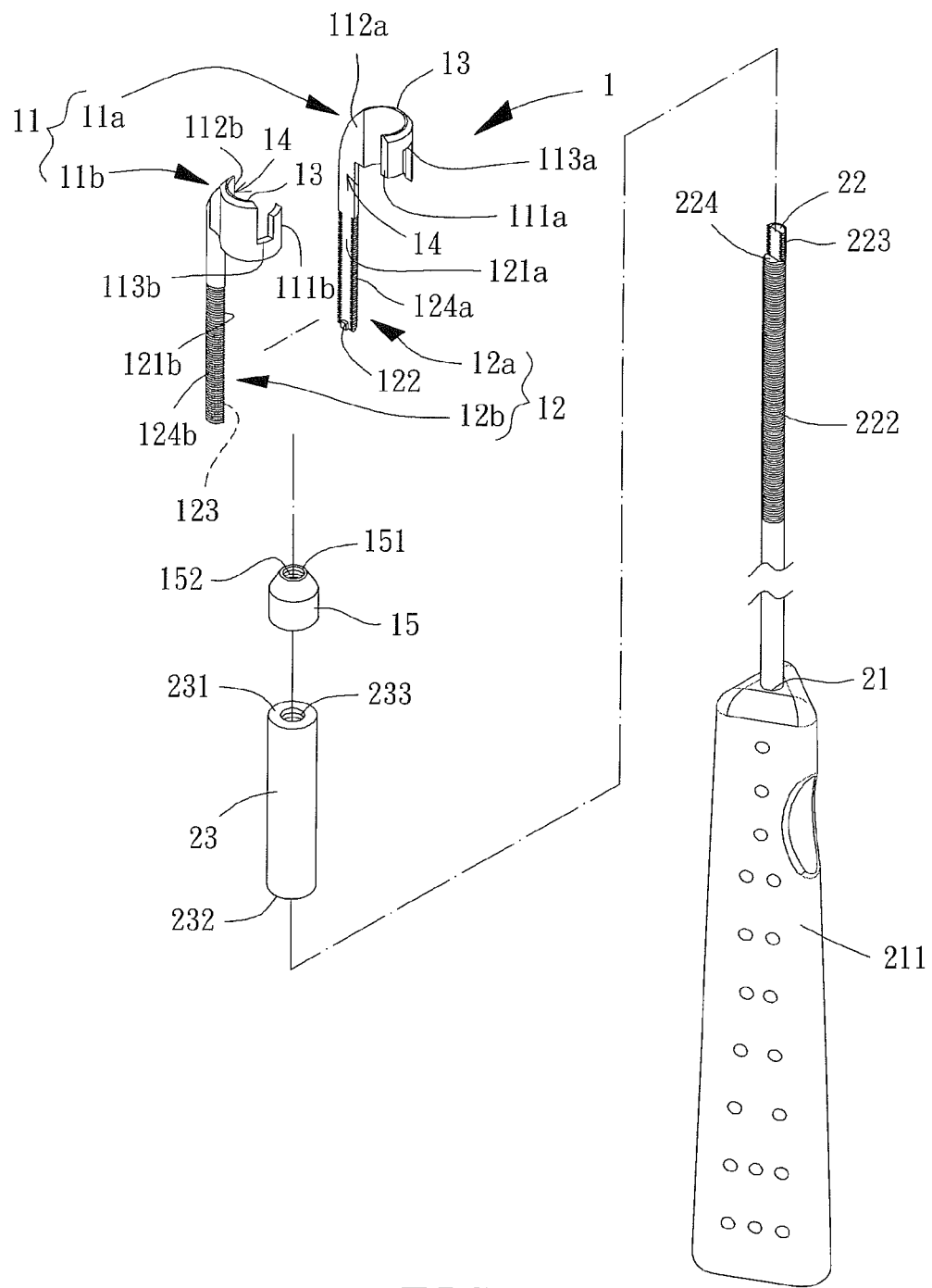
FIG. 5 is an exploded view of a tendon stripper according to a second embodiment of the present invention.

Referring to FIG. 5, the stripping device 1 can further include an auxiliary member 15 with an auxiliary hole 151 extending therethrough. As such, the assembled first and second coupling members 12a and 12b are coupled to the auxiliary member 15 via the auxiliary hole 151, allowing the first and second parts 11a and 11b to be properly aligned with each other. Based on this, the coupling effect between the first and second parts 11a and 11b can be improved, providing convenient coupling between the stripping device 1 and the rod 2.

Referring to FIG. 5, the first surface 121a of the first coupling member 12a has a positioning protrusion 122, and the second surface 121b of the second coupling member 12b has a positioning cavity 123. Once the first surface 121a is aligned with the second surface 121b, the positioning protrusion 122 of the first surface 121a can be inserted into the positioning cavity 123 of the second surface 121b, improving the positioning stability therebetween.

Referring to FIG. 2, the rod 2 has a handle end 21 and a coupling end 22 opposite to the handle end 21. A handle 211 is mounted at the handle end 21 for gripping purposes. The assembly end. 22 may couple to the coupling member 12 of the stripping device 1 by engagement, fastening or screwing. In this embodiment, the coupling end 22 has a first threaded hole 221, the first coupling member 12a of the stripping device 1 has a first thread 124a, and the second coupling member 12b of the stripping device 1 has a second thread 124b. The first and second coupling members 12a and 12b can be screwed together into the first threaded hole 221 of the coupling end 22 via the first thread 124a and the second thread 124b.

Figure 6:
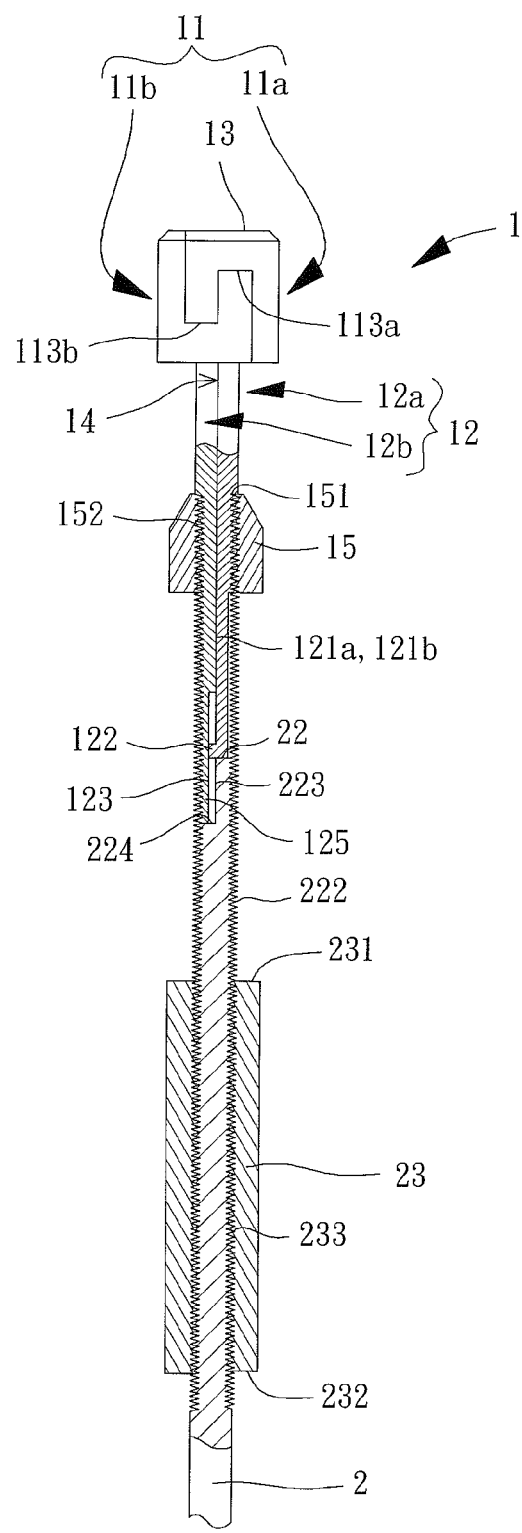
FIG. 6 is a cross sectional view of the tendon stripper according to the second embodiment of the present invention showing a fixing member coupling to a rod at a position adjacent to a handle end of the rod.
Figure 7:
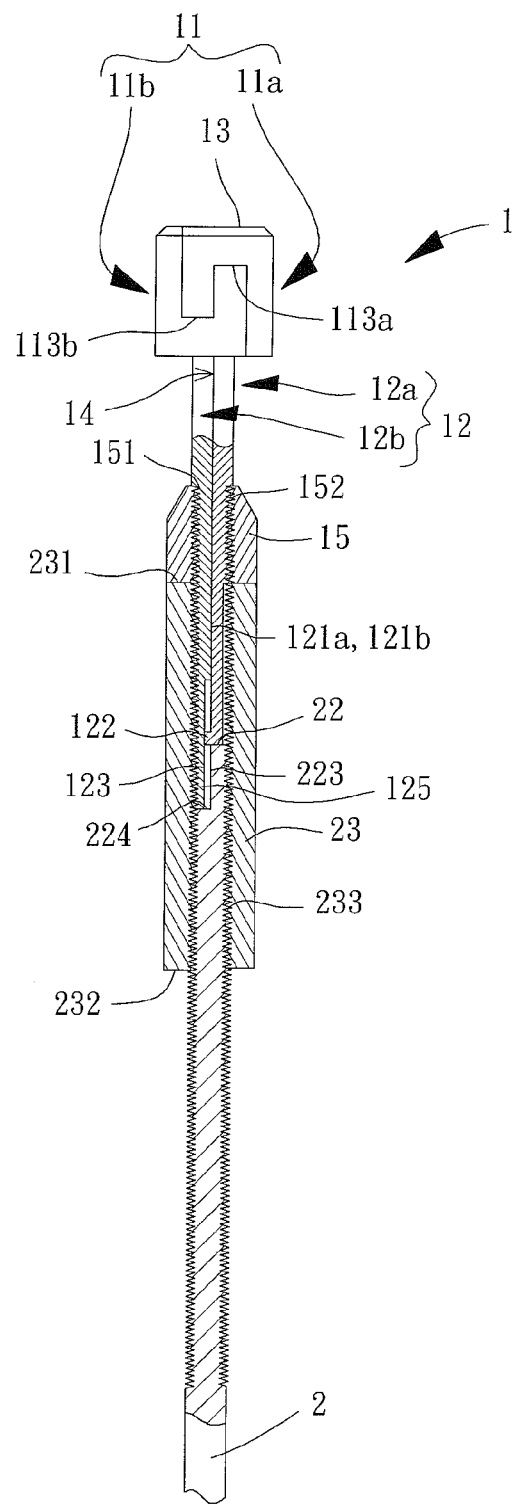
FIG. 7 is a cross sectional view of the tendon stripper according to the second embodiment of the present invention showing the fixing member coupling to the rod at a position adjacent to a coupling end of the rod.

The rod 2 can further include a fixing member 23. Referring to FIG. 5, the rod 2 can couple to the stripping device 1 via the fixing member 23. Specifically, the rod 2 can couple to the fixing member 23 by fastening, press fitting or screwing. In this embodiment, the fixing member 23 has a first end 231 and a second end 232 opposite to the first end 231. The fixing member 23 has a second threaded hole 223 extending through the first and second ends 231 and 232. The coupling end 22 of the rod 2 has a third thread 222. The coupling end 22 can be screwed into the second threaded hole 233 of the fixing member 23 via the third thread 222. Referring to FIG. 6, when the stripping device 1 couples to the rod 2 via the fixing member 23, the coupling end 22 of the rod 2 is screwed into the second threaded hole 233 of the fixing member 23 via one end of the fixing member 23. The rod 2 is screwed further into the second threaded hole 233 until the coupling end 22 of the rod 2 extends out of another end of the fixing member 23. In this regard, the coupling end 22 of the rod 2 is connected to the assembled first and second coupling members 12a and 12b. Then, the fixing member 23 can be screwed to the assembled first coupling member 12a and the second coupling member 12b as shown in FIG. 7. Therefore, the coupling end 22 of the rod 2 and the assembled first coupling member 12a and the second coupling member 12b can be screwed together inside the fixing member 23 for an improved coupling effect.

Referring to FIGS. 6 and 7, before the assembled first and second coupling members 12a and 12b are connected with the coupling end 22 of the rod 2, the assembled first and second coupling members 12a and 12b can be coupled with the auxiliary member 15 for retaining purposes. In this embodiment, the auxiliary hole 151 of the auxiliary member 15 has an auxiliary thread 152 with which the first and second screws 124a and 124b are engaged. This provides a convenient coupling mechanism for the first and second coupling members 12a and 12b before they are connected with the rod 2.

Moreover, in order to properly hold the first and second coupling members 12a and 12b together when they are connected to the coupling end 22 of the rod 2, the second coupling member 12b has a first extending portion 125 protruding from the second coupling member 12b, and the coupling end 22 of the rod 2 has a second extending portion 223 protruding from the coupling end 22. In this regard, the coupling end 22 can form a shoulder portion 224. Based on this, when the coupling end 22 of the rod 2 is aligned with and connected to the assembled first and second coupling members 12a and 12b, the first extending portion 125 abuts with the shoulder portion 224 of the coupling end 22, and the second extending portion 223 abuts with the first coupling member 12a. Accordingly, when the coupling end 22 of the rod 2 is screwed to the assembled first and second coupling members 12a and 12b, the fixing member 23 can be properly coupled with the assembled first and second coupling members 12a and 12b and the rod 2 under guidance of the first and second extending portions 125 and 223.

Figure 8:
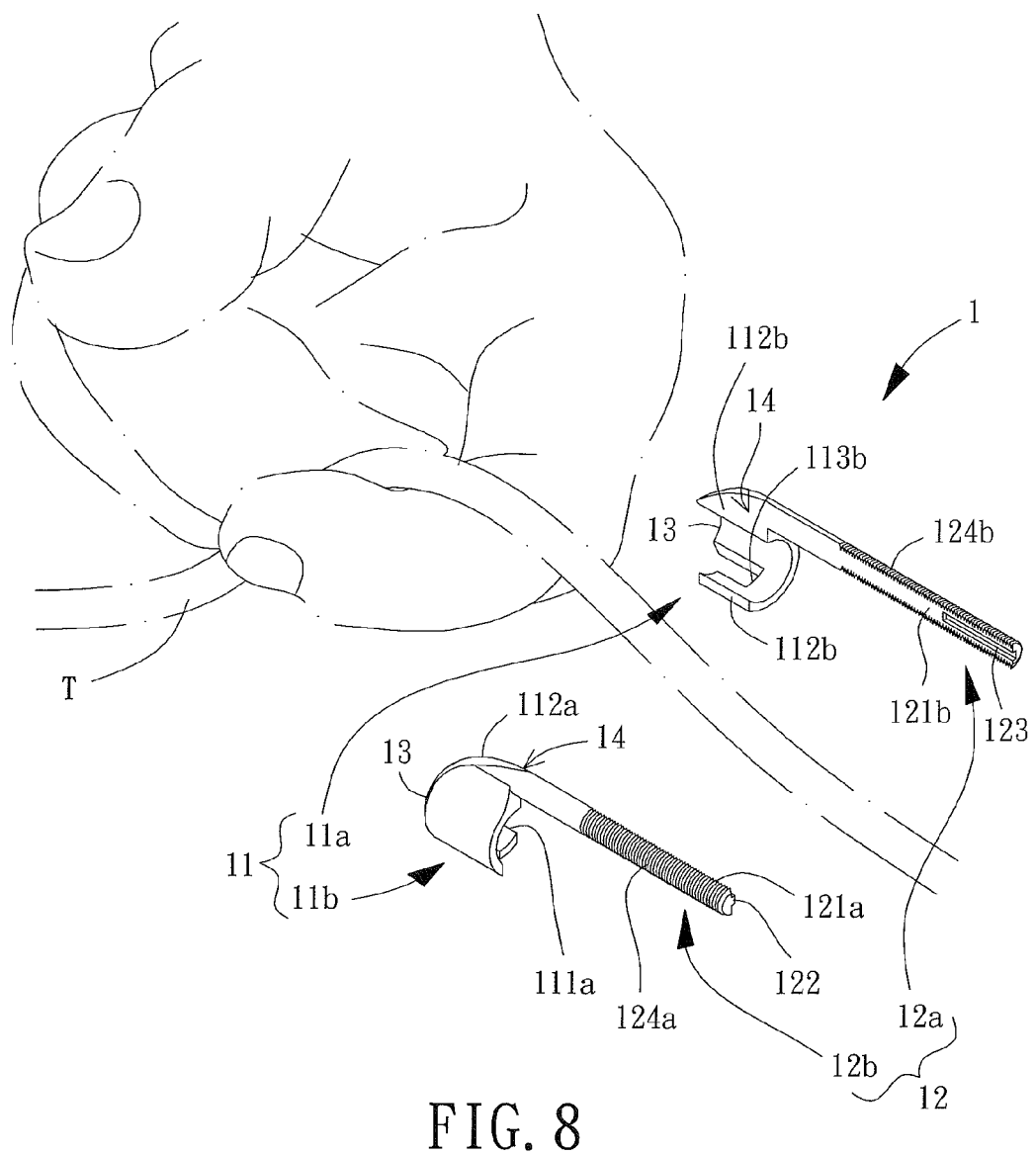
FIG. 8 is a use of the tendon stripper in removal of a tendon from a bone.

When the tendon stripper according to the present invention is used to strip a tendon "T" from a bone, a small section of the tendon "T" is pulled up as shown in FIG. 8. Then, the first part 11a of the stripping member 11 is used to receive the pulled part of the tendon "T." At this point, the pulled part of the tendon "T" is located between the first extending end 111a and the first assembly end 112a. The first and second parts 11a and 11b of the stripping member 11 are then combined to each other, such that the pulled part of the tendon "T" is located in the enclosed space formed between the first and second parts 11a and 11b of the stripping member 11. In this regard, the assembled first and second parts 11a and 11b is coupled with the rod 2 (not shown in FIG. 8), and the handle 211 of the rod 2 is pulled to move the stripping device 1 along the bone to which the tendon "T" is attached. In this manner, the tendon "T" can be stripped off the bone by the blade portion 13 of the stripping device 1.

In conclusion, the tendon stripper according to the present invention has the separating portion 14 which divides the stripping member 11 into the first part 11a and the second part 11b. The first part 11a and the second part 11b can be combined with each other to retain the tendon "T" in the enclosed space of the stripping member 11 without having to cut open the tendon "T" to form a free end in order for the free end to be extended through the stripping member 11. This advantageously avoids the generation of the incisions during the tendon transplantation and reducing the possibility of wound infection. Also, as compared with the conventional tendon stripper 9 which requires an additional instrument for retaining the free end of the tendon, the stripping device 1 according to the invention does not need to form any free end of the tendon and therefore does not rely on such an instrument, providing a convenient surgical procedure.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A tendon stripper comprising:
a stripping device comprising a stripping member, a first coupling member and a second coupling member, wherein the stripping member has a blade portion and a separating portion separating the stripping member into first and second parts wherein the first part has a first extending end and a first assembly end opposite to the first extending end, wherein the second part has a second extending end and a second assembly end opposite to the second extending end, wherein the first extending end couples to the second extending end, wherein the first assembly end couples to the second assembly end, wherein the stripping member forms an enclosed structure wherein the first coupling member couples to the first assembly end of the first part, and wherein the second coupling member couples to the second assembly end of the second part; and
a rod with a handle end and a coupling end opposite to the handle end, with the coupling end of the rod coupling to the stripping device via the first and second coupling members.

2. The tendon stripper as claimed in claim 1, wherein the first part has a first engaging portion and the second part has a second engaging portion engaging with the first engaging portion.

3. The tendon stripper as claimed in claim 1, wherein the first coupling member has a first surface, and the second coupling member has a second surface aligned with and connected to the first surface.

4. The tendon stripper as claimed in claim 3, wherein the first surface of the first coupling member has a positioning protrusion, wherein the second surface of the second coupling member has a positioning cavity, and wherein the positioning protrusion of the first surface is inserted into the positioning cavity of the second surface.

5. The tendon stripper as claimed in claim 1, wherein the first coupling member of the stripping device has a first thread, wherein the second coupling member of the stripping device has a second thread, and wherein the first coupling member and the second coupling member couple together to the coupling end of the rod via the first thread and the second thread.

6. The tendon stripper as claimed in claim 5, wherein the coupling end of the rod has a first threaded hole, wherein the first coupling member and the second coupling member are screwed together into the first threaded hole of the coupling end of the rod via the first thread and the second thread.

7. The tendon stripper as claimed in claim 5, wherein the rod has a fixing member with a first end and a second end opposite to the first end, wherein the fixing member has a threaded hole extending from the first end to the second end, wherein the coupling end of the rod has a third thread, and wherein the coupling end of the rod, the first coupling member and the second coupling member are screwed together into the fixing member.

8. The tendon stripper as claimed in claim 7, wherein the second coupling member has a first extending portion protruding from the second coupling member, wherein the coupling end of the rod has a second extending portion protruding from the coupling end, wherein a shoulder portion is formed at the coupling end, wherein the first extending portion abuts with the shoulder portion of the coupling end, and wherein the second extending portion abuts with the first coupling member.

9. The tendon stripper as claimed in claim 5, wherein the stripping device has an auxiliary member with an auxiliary hole extending through the auxiliary member, and wherein the first coupling member and the second coupling member couple together to the auxiliary member via the auxiliary hole.

10. The tendon stripper as claimed in claim 9, wherein the auxiliary hole has an auxiliary thread.

\* \* \* \* \*